United States Patent [19]

Sellstedt et al.

[11] 4,209,528

[45] Jun. 24, 1980

[54] ANTISECRETORY OXAMIC ACID ESTERS

[75] Inventors: John H. Sellstedt, Pottstown; Charles J. Guinosso, King of Prussia; Dieter H. Klaubert, Perkiomenville, all of Pa.; David A. Shriver, Martinsville, N.J.

[73] Assignee: American Home Products Corporation, New York, N.Y.

[21] Appl. No.: 1,121

[22] Filed: Jan. 5, 1979

[51] Int. Cl.² .............................................. A61K 31/275
[52] U.S. Cl. .................................................... 424/304
[58] Field of Search .......................................... 424/304

[56] References Cited

U.S. PATENT DOCUMENTS 4,091,011   5/1978   Wright .................................. 424/304

*Primary Examiner*—Frederick E. Waddell
*Attorney, Agent, or Firm*—Richard K. Jackson

[57] ABSTRACT

Variously substituted oxanilic acid esters possessing anti-secretory activity are useful anti-ulcer agents.

8 Claims, No Drawings

ANTISECRETORY OXAMIC ACID ESTERS

RELATED APPLICATIONS

This application is a continuation-in-part of Ser. No. 778,516 filed Mar. 17, 1977 now U.S. Pat. No. 4,137,325 granted Jan. 30, 1979.

SUMMARY OF THE INVENTION

In accordance with this invention there is provided a process for treating peptic ulcer disease which comprises administering to an animal suffering from peptic ulcers and N-substituted lower alkyl or phenyl ester of oxamic acid.

The anti-ulcer agents of this invention function in their anti-secretory capacity to reduce (1) total gastric volume, (2) hydrogen ion secretion, or (3) hydrogen ion concentration. The reduction of any one of these parameters aids in attenuating the general debilitating influence of a peptic ulcer.

DETAILED DESCRIPTION OF THE INVENTION

The anti-secretory agents useful in the process of this invention are the following N-substituted lower alkyl or phenyl oxamic acid esters in which the N-substituent is:
2-cyano-3-aminophenyl-;
2-cyano-3-methylaminophenyl-;
2-cyano-3-dimethylaminophenyl-;
2-cyano-3-ethylmethylaminophenyl-;
2-cyano-3-diethylaminophenyl-;
3-cyano-5-nitrophenyl-;
2-cyano-3-pentyloxyphenyl-;
2-cyano-3-(1-pyrrolidinyl)phenyl-;
2-cyano-3-(4-morpholinyl)-5-trifluoromethylphenyl-;
or
2-cyano-3-piperidinophenyl-.

The expression "lower alkyl" employed throughout this application is intended to embrace those alkyl groups having from 1 to 6 carbon atoms and preferably from 1 to 4 carbon atoms.

Each of the compounds disclosed was found active in the following scientifically recognized, standard test for anti-secretory activity:

Male Charles River rats weighing 190–260 grams are deprived of food but not water for 18 hours prior to use. Water is, however, withheld during the experiment. The rats are weighed, anesthetized with ether and the pylorus ligated according to the method of Shay et al., Gastroenterology 26: 906–913 (1954). Treatment or vehicle control is then administered interduodenally (i.d.). Rats are housed two per cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or blood are eliminated. An aliquot of each is frozen for later analysis of pepsin. The pH is measured and 1 ml. of gastric juice is titrated with 0.1N NaOH to a pH of 7.0–7.4. The data are analyzed by an analysis of variance and using the pooled error variance to make t-comparisons between groups.

The use of compounds exhibiting anti-secretory activity in the curative and/or prophylactic treatment of peptic ulcer disease is an established, beneficial procedure.

The potency of each compound is reported at the end of the example illustrating its production. The potency reported is the lowest dose administered at which two of the three parameters (a) total gastric volume, (b) hydrogen ion secretion, and (c) hydrogen ion concentration, were significantly decreased.

EXAMPLE 1

(3-Amino-2-cyanophenylamino)oxoacetic acid ethyl ester

A mixture of 11.5 g. of (3-nitro-2-cyanophenylamino) oxoacetic acid ethyl ester, 4.4 g. of 10% Pd/C and 18 g. of cyclohexene in 220 ml. of ethanol is refluxed for 35 minutes, filtered through celite and evaporated to dryness. The residue is chromatographed on silican gel with chloroform and the title compound is recrystallized from ethanol, m.p. 133–136° C.

Anal. Calcd. for $C_{11}H_{11}N_3O_3$: C, 56.65; H, 4.76; N, 18.02. Found: C, 56.58; H, 4.64; N, 18.20. Potency: 10 mg./kg.

(3-Nitro-2-cyanophenylamino)oxoacetic acid ethyl ester is prepared by condensing 2-amino-6-nitrobenzonitrile with ethyl oxalylchloride in 100 ml. methylene chloride in the presence of pyridine at about 10° C. Aqueous work-up and evaporation of methylene chloride followed by recrystallization from ethanol yields the desired intermediate, m.p. 111°–113° C.

Anal. Calcd. for $C_{11}H_9N_3O_5$: C, 50.19; H, 3.45; N, 15.97. Found: C, 50.11; H, 3.44; N, 15.99.

2-Amino-6-nitrobenzonitrile is obtained by iron reduction of 2,6-dinitrobenzonitrile in methanolic HCl. The mixture is stirred for 0.5 hr., diluted with water and the benzonitrile is extracted with methylene chloride, dried and evaporated in vacuo to yield the desired intermediate, m.p. 195°–197° C.

Anal. Calcd. for $C_7H_5N_3O_2$: C, 51.54; H, 3.09; N, 25.76. Found: C, 50.94; H, 2.98; N, 25.66.

EXAMPLE 2

[3-(Methylamino)-2-cyanophenylamino]oxoacetic acid ethyl ester

Oxalation of 2-amino-6-methylaminobenzonitrile as in Example 1 gives the title compound, m.p. 137°–139° C.

Anal. Calcd. for $C_{12}H_{13}N_3O_3$: C, 58.29; H, 5.30; N, 17.00. Found: C, 58.13; H, 5.32; N, 16.94. Potency: 10 mg/kg.

2-Amino-6-methylaminobenzonitrile is prepared by iron reduction of 2-methylamino-6-nitrobenzonitrile as in Example 1.

2-Methylamino-6-nitrobenzonitrile is prepared as follows:
to 19.3 g. of 2,6-dinitrobenzonitrile in 150 ml. of dimethylformamide at 85° C. is added 25 ml. of 40% aqueous methylamine. The mixture is heated for 1 hour, poured into ice water and the product is removed by filtration, m.p. 203°–206° C.

Anal. Calcd. for $C_8H_7N_3O_2$: C, 54,23; H, 3.99; N, 23.72. Found: C, 54.24; H, 3.70; N, 24.02.

EXAMPLE 3

[2-Cyano-3-dimethylaminophenylamino]oxoacetic acid ethyl ester

To a solution of 3.4 g. of crude 2-amino-6-dimethylaminobenzonitrile and 1.6 g. of pyridine in 50 ml. of methylene chloride at 0° C. is added dropwise 2.7 g. of ethyl oxalyl chloride in 25 ml. of methylene chloride. The solution is stirred at 0° C. for 3 hr., warmed to room temperature and water is added. The organic phase is separated, dried and evaporated to give a yellow solid which is recrystallized from benzene-hexane to yield 3.2 g. of pure product, m.p. 124°–126° C.

Anal. Calcd. for $C_{13}H_{15}N_3O_3$: C, 59.76; H, 5.74; N, 16.08. Found: C, 59.47; H, 5.74; N, 16.08. Potency: 20 mg./kg.

The crude benzonitrile is prepared in the following way:

To a suspension of 5.7 g. of 2-dimethylamino-6-nitrobenzonitrile in 20 ml. of methanol and 17 ml. of conc. hydrochloric acid is added 5.3 g. of iron powder in portions. The mixture is stirred for ½ hr., diluted with 200 ml. of water and extracted with methylene chloride which is dried and evaporated in vacuo to yield crude benzonitrile.

EXAMPLE 4

[3-(Ethylmethylamino)-2-cyanophenylamino]oxoacetic acid ethyl ester

Treatment of 2amino-6-(ethylmethylamino)benzonitrile with oxalyl chloride as in Example 1 gives the product, m.p. 75°–78° C.

Anal. Calcd. for $C_{14}H_{17}N_3O_3$: C, 61.08; H, 6.22; N, 15.25. Found: C, 60.77; H, 6.21; N, 15.34. Potency: 20 mg./kg.

The amine is obtained by the usual iron reduction. 2-(ethylmethylamine)-6-nitrobenzonitrile is obtained by displacement with ethylmethylamine, m.p. 60°–63° C.

Anal. Calcd. for $C_{10}H_{11}N_3O_2$: C, 58.53; H, 5.40; N, 20.48, Found: C, 58.84; H, 5.48; N, 20.81.

EXAMPLE 5

[2-cyano-3-(diethylamino)phenylamino]oxoacetic acid ethyl ester

Treatment of 2-amino-6-diethylamino-benzonitrile with ethyl oxalyl chloride as in example 1 yields the title compound, m.p. 57°–59° C.

Anal. Calcd. for $C_{15}H_{19}N_3O_3$: C, 62.27; H, 6.62; N, 14.52. Found: C, 62.23; H, 6.43; N, 14.62. Potency: 1 mg./kg.

2-amino-6-diethylaminobenzonitrile is prepared by cyclohexene - Pd/C reduction of the corresponding nitro compound similar to example 1. The crude amine is used directly.

2-diethylamino-6-nitrobenzonitrile is prepared as follows:

To an equimolar mixture of ethyl iodide and 2-ethylamino-6-nitrobenzonitrile in DMF is added an equimolar amount of sodium hydride (50% in oil). After 1 hr., the reaction is poured into water and extracted with methylene chloride. The dried extracts are passed through silican gel to give the desired product which is recrystallized from hexane, m.p. 39°–41° C.

Anal. Calcd. for $C_{11}H_{13}N_3O_2$: C, 60.26; H, 5.98; N, 19.19. Found: C, 59.82; H, 5.97; N, 18.88.

2-ethylamino-6-nitrobenzonitrile is prepared from 2,6-dinitrobenzonitrile and ethylamine following the procedure in the last paragraph of example 10, infra.

EXAMPLE 6

(3-Cyano-5-nitrophenylamino)oxoacetic acid ethyl ester 3-amino-5-nitrobenzonitrile is oxalated as in example 1 to give the title compound, m.p. 114°–116° C.

Anal. Calcd. for $C_{11}H_9N_3O_5$: C, 50.19; H, 3.45; N, 15.97. Found: C, 50.29; H, 3.42; N, 16.06. Potency: 25 mg./kg.

3-amino-5-nitrobenzonitrile is prepared by iron reduction of 3,5-dinitrobenzonitrile as in example 1, m.p. 168°–170° C.

Anal. Calcd. for $C_7H_5N_3O_2$: C, 51.53; H, 3.09; N, 25.76. Found: C, 51.30; H, 3.03; N, 25.84.

EXAMPLE 7

[(2-cyano-3-pentyloxyphenyl)amino]oxoacetic acid ethyl ester 2-amino-6-pentyloxybenzonitrile is oxalated as in example 1, m.p. 78°–81° C.

Anal. Calcd. for $C_{16}H_{20}N_2O_4$: C, 63.14; H, 6.62; N, 9.21. Found: C, 62.99; H, 6.67; N, 9.18. Potency: 5 mg./kg.

2-amino-6-pentyloxybenzonitrile is prepared by Pd/C cyclohexene reduction of 2-nitro-6-pentyloxybenzonitrile as in example 1, m.p. 70°–73° C.

Anal. Calcd. for $C_{12}H_{16}N_2O$: C, 70.56; H, 7.90; N, 13.72. Found: C, 70.40; H, 7.70; N, 13.63.

2-nitro-6-pentyloxybenzonitrile is known: A. Russell and L. M. Addison, J. Am. Chem. Soc. 65, 2379 (1943).

EXAMPLE 8

[2-cyano-3-(1-pyrrolidinyl)phenylamino]oxoacetic acid ethyl ester

Prepared as in example 1, m.p. 138°–141° C.

Anal. Calcd. for $C_{15}H_{17}N_3O_3$: C, 62.70; H, 5.96; N, 14.63. Found: C, 62.81; H, 5.98; N, 14.61. Potency: 20mg./kg.

2-amino-6-pyrrolidinylbenzonitrile is prepared by iron reduction as in example 1, m.p. 112°–114° C.

Anal. Calcd. for $C_{11}H_{13}N_3$: C, 70.56; H, 7.00; N, 22.44. Found: C, 70.51; H, 6.71; N, 22.50.

2-nitro-6-pyrrolidinylbenzonitrile is prepared from pyrrolidine and 2,6-dinitrobenzonitrile as in example 10, m.p. 110°–112° C.

Anal. Calcd. for $C_{11}H_{11}N_3O_2$: C, 60,82; H, 5.10; N, 19.35. Found: C, 61.04; H, 5.14; N, 19.49.

EXAMPLE 9

[2-cyano-3-(4-morpholinyl)-5-(trifluoromethyl)-phenylamino]oxoacetic acid ethyl ester 2-amino-4-trifluoromethyl-6-morpholinylbenzonitrile is oxalated in the usual manner, m.p. 106°–109° C.

Anal. Calcd. for $C_{16}H_{16}N_3O_4F_3$: C, 51.76; H, 4.34; N, 11.32. Found: C, 52.07; H, 4.40; N, 11.33. Potency: 25 mg/kg.

2-amino-4-trifluoromethyl-6-morpholinylbenzonitrile is prepared by cyclohexene - Pd/C reductiion as in example 1, m.p. 166°–171° C.

Anal. Calcd. for $C_{12}H_{12}N_3OF_3$: C, 53.14; H, 4.46; N, 15.49. Found: C, 53.01; H, 4.43; N, 15.38.

2-nitro-4-trifluoromethyl-6-morpholinylbenzonitrile is prepared from 2,6-dinitro-4-trifluoromethylbenzonitrile and morpholine as in example 10, m.p. 174°–178° C.

2,6-dinitro-4-trifluoro-4-trifluoromethylbenzonitrile is known: J. R. Beck, J. Org. Chem. 37, 3224 (1972).

EXAMPLE 10

[2-Cyano-3-(1-piperidinyl)phenylamino]oxoacetic acid ethyl ester

This is prepared from 2-amino-6-(1-piperidinyl)-benzonitrile in a manner analogous to the preparation given in Example 1, m.p. 98°–100° C.

Anal. Calcd. for $C_{16}H_{19}N_3O_3$: C, 63.77; H, 6.36; N, 13.94. Found: C, 63.76; H, 6.37; N, 13.76. Potency: 20 mg./kg.

2-Amino-6-(1-piperdinyl)benzonitrile is prepared from 2-nitro-6-(1-piperidinyl)benzonitrile as in example 1 by iron reduction.

2-Nitro-6-(1-piperidinyl)benzonitrile is prepared as follows:

To a solution of 19.3 g. of 2,6-dinitrobenzonitrile in 300 ml. of DMF is added 25.5 g. of piperidine and the resulting solution is warmed to 85° C. and kept at that temperature until the reaction is complete. The reaction mixture is poured into water, the product is filtered and dried, m.p. 119°–121° C.

Anal. Calcd. for $C_{12}H_{13}N_3O_2$: C, 62.32; H, 5.67; N, 18.17. Found: C, 62.32; H, 5.82; N, 18.26.

The anti-secretory agents of this invention may be administered orally of parenterally. Liquid compositions include sterile solutions for parenteral administration as well as suspensions, emulsions, syrups and elixirs of the active ingredients for oral administration. The compounds may be employed alone as the sole basis for treatment or they may be advantageously employed in conjunction with a treatment regimen utilizing a conventional antacid such as calcium carbonate, magnesium carbonate, bismuth carbonate, aluminum or magnesium hydrated oxides, magnesium glycinate, magnesium trisilicate, calcium trisilicate, or sodium bicarbonate to maintain gastric acidity from about a pH of 3 to 5 or higher. Likewise, the anti-seccretory agents of this invention may be used in conjunction with anti-cholinergic agents or $H_2$-receptor blocking agents.

Pharmaceutical compositions containing the anti-secretory agents of this invention are formulated conventionally with a solid or liquid carrier. Solid carriers acceptable for use in the administration of anti-secretory agents via tablets, capsules or powders, include magnesium carbonate, magnesium stearate, talc, sugar, lactose, pectin, dextrin, starch, gelatin, tragacanth, methyl cellulose, sodium carboxymethyl cellulose, low melting waxes and cocoa butter. Additional optional ingredients include flavoring agents, lubricants, solubilizers, suspending agents, binders and disintegrants. The quantity of active anti-secretory agents in a solid or liquid composition may be varied widely, such as from about 10 to 80 percent or more.

Unit dosage forms containing from about 10 to 500 milligrams of the substituted oxamic acid esters are especially suitable for use in oral administration.

What is claimed is:

1. A process for treating peptic ulcer disease which comprises administering to a mammal in need thereof an N-substituted lower alkyl or phenyl ester of oxamic acid in which the N-substituent is:
   2-cyano-3-aminophenyl-;
   2-cyano-3-methylaminophenyl-;
   2-cyano-3-dimethylaminophenyl-;
   2-cyano-3-ethylmethylaminophenyl-;
   2-cyano-3-diethylaminophenyl-;
   3-cyano-5-nitrophenyl-;
   or
   2-cyano-3-pentyloxyphenyl-.

2. A process of claim 1 in which said oxamic acid ester is ethyl 3-amino-2-cyano-oxanilate.

3. A process of claim 1 in which said oxamic acid ester is ethyl 2-cyano-3-methylamino-oxanilate.

4. A process of claim 1 in which said oxamic acid ester is 2-cyano-3-dimethylamino-oxanilate.

5. A process of claim 1 in which said oxamic acid ester is 2-cyano-3-ethylmethylamino-oxanilate.

6. A process of claim 1 in which said oxamic acid ester is 2-cyano-3-diethylamino-oxanilate.

7. A process of claim 1 in which said oxamic acid ester is 3-cyano-5-nitro-oxanilate.

8. A process of claim 1 in which said oxamic acid ester is 2-cyano-3-pentyloxy-oxanilate.

* * * * *